US00PP11651P

United States Patent [19]

Trees

[11] Patent Number: Plant 11,651

[45] Date of Patent: Nov. 28, 2000

[54] NEW GUINEA IMPATIENS PLANT NAMED 'BALCELELRO'

[75] Inventor: Scott C. Trees, Nipomo, Calif.

[73] Assignee: Ball Floraplant, a division of Ball Horticultural Co., West Chicago, Ill.

[21] Appl. No.: 09/253,790

[22] Filed: Feb. 20, 1999

[51] Int. Cl.[7] ..... A01H 5/00

[52] U.S. Cl. ..... Plt./318

[58] Field of Search ..... Plt./318

[56] References Cited

U.S. PATENT DOCUMENTS

| | | | |
|---|---|---|---|
| P.P. 6,684 | 3/1989 | Kientzler | Plt./318 |
| P.P. 6,686 | 3/1989 | Kientzler | Plt./318 |
| P.P. 8,358 | 8/1993 | Bull | Plt./318 |

*Primary Examiner*—Bruce R. Campbell
*Assistant Examiner*—Kent L. Bell
*Attorney, Agent, or Firm*—C. A. Whealy

[57] ABSTRACT

A new and distinct cultivar of New Guinea Impatiens plant named 'Balcelelro', characterized by its reddish purple-colored flowers; floriferousness; upright and mounded plant habit; relatively tall plant size; vigor; good basal branching; and dark brown leaves.

1 Drawing Sheet

BACKGROUND OF THE INVENTION

The present invention relates to a new and distinct cultivar of New Guinea Impatiens plant, botanically known as *impatiens hawkeri,* and hereinafter reffered to by the cultivar name 'Balcelelro'.

The new Impatiens is a product of a planned breeding program conducted by the Inventor in Arroyo Grande, Calif. The objective of the breeding program was to develop new cultivars with excellent basal branching, medium upright growth habit, numerous large flowers, and interesting flower and foliage colors.

The new Impatiens orginated from a cross made by the Inventor of two unnamed proprietaty *Impatiens hawkeri* selections. The cultivar 'Balcelelro' was discovered and selected by the Inventor as a flowering plant within the progeny of the stated cross in a controlled environment in Arroyo Grande, Calif., in December, 1996.

Asexual reproduction of the new cultivar by terminal cuttings taken at Arroyo Grande, Calif., has shown that the unique features of this new Impatiens are stable and reproduced true to type in successive generations of asexual reproduction.

SUMMARY OF THE INVENTION

The following traits have been repeatedly observed and are determined to be the unique characteristics of 'Balcelelro'. These characteristics in combination distinguish 'Balcelelro' as a new and distinct cultivar:

1. Reddish purple-colored flowers; very freely flowering.
2. Upright and mounded plant habit.
3. Relatively tall plant size; vigorous.
4. Good basal branching.
5. Dark brown leaves.

The new Impatiens can be compared to the *Impatiens hawkeri* cultivar 'BSR-221 Electric Pink', disclosed in U.S. Plant Pat. No. 8,399. However, in side-by-side comparisons conducted in Arroyo Grande, Calif., plants of the new Impatiens differ from plants of the cultivar 'BSR- 221 Electric Pink' in the following characteristics:

1. Plants of the new Impatiens have larger leaves than plants of the cultivar 'BSR-221 Electric Pink'.

2. Leaves of plants of the new Impatiens are more rugose and glossier than leaves of plants of the cultivar 'BSR-221 Electric Pink'.

3. Upper leaf surface of plants of the new Impatiens are dark brown in color whereas upper leaf surfaces of plants of the cultivar 'BSR-221 Electric Pink' are green in color.

4. Flower color of plants of the new Impatiens is darker than flower color of plants of the cultivar 'BSR-221 Electric Pink'.

A detailed comparison of plants of the cultivar 'Balcelelro' and the cultivar 'BSR-221 Electric Pink' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of 'Balcelelro'. Flower and foliage colors in the photograph may appear different than the actual colors due to light reflectance.

DETAILED BOTANICAL DESCRIPTION

The cultivar 'Balcelelro' has not been observed under all possible environmental conditions. The phenotype may vary somewhat with variations in environment such as temperature and light intensity, without, however, any variance in genotype. The following observations, measurements and comparisons describe plants in 10-cm pots in Arroyo Grande, Calif., under commercial practice in a glass-covered greenhouse with day temperatures about 20 to 22° C, night temperatures about 18 to 20° C., and light levels generally about 2,500 to 3,000 footcandles.

In following description, color references are made to The Royal Horticultural Society Colour Chart except where general terms of ordinary dictionary significance are used.

Botanical classification: *Impatiens hawkeri* cultivar 'Balcelelro'.

Parentage:

*Male parent.*—Unnamed proprietary *Impatiens hawkeri* selection.

*Female parent.*—Unnamed proprietary *Impatiens hawkeri* selection.

Propagation:

*Type cutting.*—Terminal cuttings.

*Time to initiate roots.*—About 7 days at 18° C.

*Time to develop roots.*—About 21 days at 18° C.

*Rooting habit.*—Fibrous, fine, freely branching.

Plant description:

*General appearance.*—Upright and mounded; relatively tall plant size; vigorous. Appropriate for 10 and 12.5-cm containers.

*Growth and branching habit.*—Good basal branching with about six to eight lateral branches at the base, dense and bushy growth. Pinching, that is, removal of the terminal apices, is usually not required.

*Crop time.*—Starting with a rooted cutting, about ten weeks are required to produce a finished flowering plant in a 10-cm container.

*Plant height.*—About 17 to 20 cm.

*Plant width.*—About 19 to 22 cm.

*Lateral branches.*—Length: About 11 to 15 cm. Diameter: About 9 mm. Internode length: About 3 to 3.5 cm. Color: 187A.

*Foliage description.*—Leaves simple, generally symmetrical, abundant, in whorls or opposite. Length: About 8.5 to 9.5 cm. Width: About 3 to 3.5 cm. Shape: Elliptic Apex: Acuminate. Base: Attenuate. Margin: Serrate with ciliation. Texture: Rugose; glossy; glabrous. Color: Young foliage, upper surface: Close to 200A. Young foliage. lower surface: 187A. Fully expanded foliage, upper surface: Close to 200A. Fully expanded foliage, lower surface: 187B. Venation, lower surface: 187B. Petiole: Length: About 1 to 1.5 cm. Diameter: About 3 to 4 mm. Color: 187C.

Flower description:

*Flower type and habit.*—Reddish purple-colored flowers. very freely and continuously flowering. flowers arise from leaf axils. Usually about ten to fifteen flowers and flower buds per lateral branch. Flowers positioned mostly above the foliage and typically face outward to upward. Flowers generally flat and rounded. Flowers persistent.

*Flowering season.*—Year-round under greenhouse conditions. In the garden, flowering is continuous from spring until fall.

*Flower longevity.*—Flowers last about one week depending on temperature, light level, and water status.

*Flower size.*—Diameter: About 6.5 to 7 cm. Depth: About 1 cm.

*flower buds.*—Length: About 2.3 cm. Diameter: About 1.4 cm. Shape: Elliptic. Color: 59A.

*Petals.*—Quantity: Five, overlapping. Length: About 3.2 to 4.3 cm. Width: About 3.5 to 4.3 cm. Shape: Cordate. Apex: Retuse. Base: Attenuate. Margin: Entire. Texture: Smooth. Color: Fully opened, upper surface: Close to 58A, iridescent; lighter towards flower center, close to white 155D overlain with close to 58A; iridescent. Fully opened, lower surface: 58B, iridescent. Fading to, upper surface: 66C, iridescent.

*Spur.*—Length: About 5 to 6 cm. Shape: Narrow and curved. Color: 185A.

*Peduncles.*—Length: About 5 cm. Angle: About 45° to the lateral branch. Strength: Moderately strong. Color: 187B.

*Reproductive organs.*—Androecium: Stamen number: Five, anthers fused, filaments free. Anther shape: Obovate. Pollen amount: Moderate. Pollen color: 11C. Gynocium: Five-loculate fused. Stigma color: 57A. Ovary color: 187A.

Disease resistance: Resistance to pathogens common to Impatiens has not been observed.

Seed development: Seed production has not been observed.

CHART A

| CHARACTERISTIC | 'BALCELELRO' | 'BSR-221 ELECTRIC PINK' |
|---|---|---|
| PLANT HEIGHT | About 17 to 20 cm | About 19 to 20 cm |
| PLANT WIDTH | About 19 to 22 cm | About 19 to 22 cm |
| LEAF SHAPE | Elliptic | Lanceolate |
| LEAF LENGTH | About 8.5 to 9.5 cm | About 7 to 7.5 cm |
| LEAF WIDTH | About 3 to 3.5 cm | About 2 to 3 cm |
| LEAF TEXTURE | Rugose; glossy; glabrous | Slightly rugose; dull; glabrous |
| LEAF COLOR UPPER SURFACE | Close to 200A | Between 137A and 147A |
| LEAF COLOR LOWER SURFACE | 187B | 200B |
| FLOWER DIAMETER | About 6.5 to 7 cm | About 6 to 6.5 cm |
| PETAL COLOR, FULLY OPENED, UPPER SURFACE | Close to 58A, iridescent; lighter towards center, close to white 155D overlain with close to 58A; iridescent | 58C; lighter towards center |
| PETAL COLOR, FULLY OPENED, LOWER SURFACE | 58B, iridescent | 58D; |
| PETAL COLOR, FADING TO | 66C, iridescent | 66D |

It is claimed:

1. A new and distinct cultivar of New Guinea Impatiens plant named 'Balcelelro', as illustrated and described.

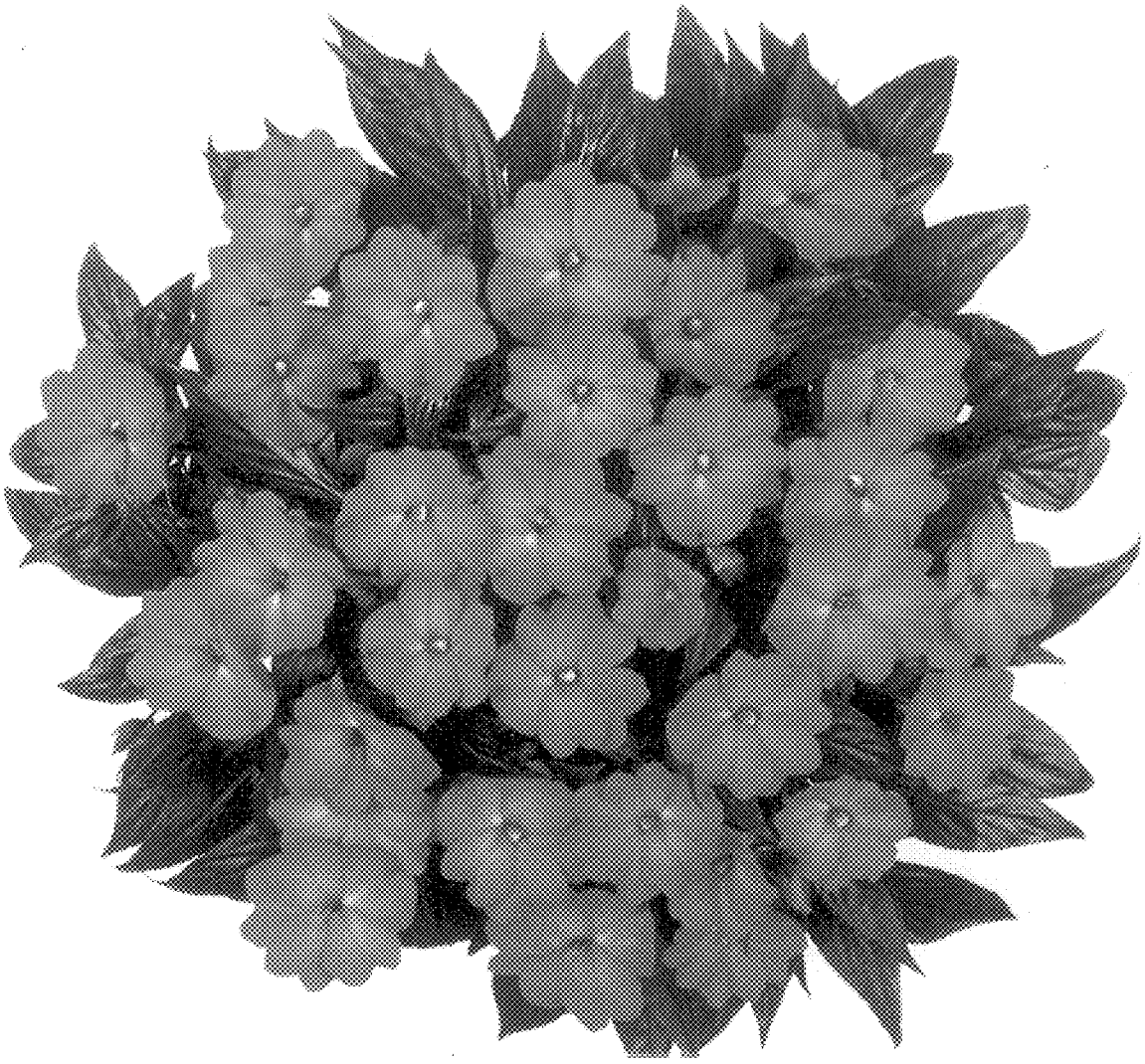

* * * * *